United States Patent [19]

Kraus

[11] Patent Number: 5,466,800
[45] Date of Patent: Nov. 14, 1995

[54] PROCESS FOR THE PREPARATION OF 2,5-DISUBSTITUTED PYRIDINES

[75] Inventor: Helmut Kraus, Köln, Germany

[73] Assignee: Bayer Aktiengesellschaft, Leverkusen, Germany

[21] Appl. No.: 87,641

[22] Filed: Jul. 6, 1993

[30] Foreign Application Priority Data

Jul. 13, 1992 [DE] Germany ............ 42 23 013.6

[51] Int. Cl.[6] ............ C07D 413/04; C07D 401/04; C07D 213/09; C07D 211/06
[52] U.S. Cl. ............ 544/82; 544/124; 544/360; 546/193; 546/250; 546/281
[58] Field of Search ............ 546/250, 281, 546/360, 193; 544/124, 82

[56] References Cited

U.S. PATENT DOCUMENTS

| | | | |
|---|---|---|---|
| 4,319,024 | 3/1982 | Peeters et al. ............ | 544/103 X |
| 4,348,396 | 9/1982 | Kierstead et al. ............ | 514/257 |
| 4,405,552 | 9/1983 | Miesel ............ | 546/309 X |
| 4,849,432 | 7/1989 | Shiokawa et al. ............ | 514/341 |

FOREIGN PATENT DOCUMENTS

| | | | |
|---|---|---|---|
| 0060071 | 9/1982 | European Pat. Off. ............ | 546/309 |
| 018473 | 12/1982 | European Pat. Off. ............ | 558/462 |
| 108483 | 9/1983 | European Pat. Off. ............ | 546/278 |
| 162464 | 5/1985 | European Pat. Off. . | |
| 235725 | 2/1987 | European Pat. Off. ............ | 546/278 |
| 0240010 | 10/1986 | Germany ............ | 546/304 |

OTHER PUBLICATIONS

S. Marchalin et al., "The Use of 4-R[1]-Benzylidene ... and 2-Amino-4H-Pyrans", Collection Czechoslovak Chem. Commun., vol. 48, pp. 3123–3129 (1983).

H. U. Sieveking et al., "Preparation of Enamino ... with LiAlH$_4$", Angew. Chem. internat. Edit., vol. 8, p. 458 (1969).
Y. Akiyama et al., "Studies on Conjugated ... with Enamines", Chem. Pharm. Bull., vol. 32(7), pp. 2821–2824 (1984).
J. P. Ferris et al., "Photochemcial Reactions ... Nicotinamide Derivatives", Science, vol. 166, pp. 765–766 (1969).
Tetrahedron (24) (1968), pp. 3369–3378.
Synthesis 1985, pp. 1116–1118.

*Primary Examiner*—Alan L. Rotman
*Attorney, Agent, or Firm*—Sprung Horn Kramer & Woods

[57] ABSTRACT

2,5-Disubstituted pyridines of the formula

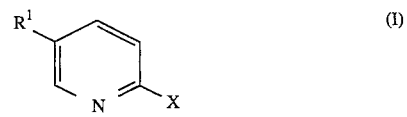

can be prepared by reacting enamines of the formula

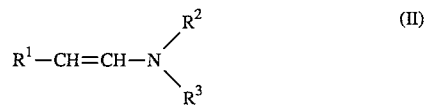

with β-amino-acrylonitriles of the formula

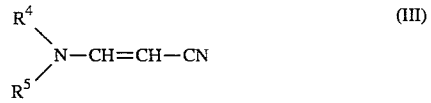

and treating the open-chain intermediate, which represents a R-R[1]-5-amino-penta-2,4-dienonitrile, with protic acids or with ammonia.

15 Claims, No Drawings

PROCESS FOR THE PREPARATION OF 2,5-DISUBSTITUTED PYRIDINES

BACKGROUND OF THE INVENTION

1. Field of the Invention

The invention relates to a process for the preparation of 2,5-disubstituted pyridines by reaction of enamines with β-amino-acrylonitriles, followed by cyclisation of the open-chain intermediate with protic acids or ammonia.

2,5-Disubstituted pyridines are important intermediates for the preparation of herbicides (EP 108,483), insecticides (EP 235,725) and pharmaceuticals (CA 1,189,509, which is equivalent to DE-OS (German Published 2,812,585 and DE-OS (German Published Specification) 2,812,586).

2. Description of the Related Art

The required 2,5-disubstituted pyridines can be obtained either by ring-closure reactions or by substitution of 3-alkyl-pyridines. However, the latter synthesis involves unavoidable formation of positional isomers.

An interesting approach is the joining together into a ring of morpholinopropene and acrylic acid derivatives, that is a reaction of $C_2$ and $C_3$ building blocks. However, the dihydropyridines obtainable by this reaction have to be aromatised by a complicated procedure (EP 108,483). The use of α-chloro-acrylonitrile (EP 162,464) leads directly to 2-chloro-5-methyl-pyridine in low yield.

The reaction of $C_4$- and higher enamines with α-chloro-acrylonitrile is described in Tetrahedron 24 (1968), 3369. However, it is plain that secondary reactions are taking place; a satisfactory yield is obtainable only at very low temperatures, which are expensive to achieve under industrial conditions (Synthesis 1985, 1116). Considering these references, it was therefore surprising that the open-chain intermediates of 4-$R^1$-5-amino-penta-2,4-dienonitriles, which can be cyclised to give the corresponding 2,5-disubstituted pyridines, are obtainable in a simple manner by using β-aminoacrylonitriles.

SUMMARY OF THE INVENTION

The invention relates to a process for the preparation of 2,5-disubstituted pyridines of the formula

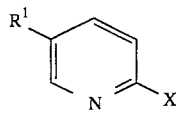  (I)

which is characterised by the reaction of 0.2–5 mol, preferably 0.4–3 mol, particularly preferably 0.7–1.5 mol, of an enamine of the formula

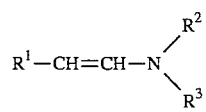  (II)

with 1 mol of a β-amino-acrylonitrile of the formula

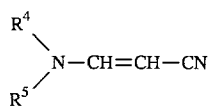  (III)

in which formulae $R^1$, $R^2$, $R^3$, $R^4$ and $R^5$, independently of one another, represent straight-chain or branched $C_1$-$C_8$-alkyl, $C_2$-$C_8$-alkenyl, $C_2$-$C_8$-alkoxyalkyl, $C_3$-$C_8$-alkoxyalkenyl, $C_3$-$C_8$-cycloalkyl, $C_6$-$C_{12}$-aryl, $C_7$-$C_{10}$-aralkyl or a 5- to 8-membered saturated or unsaturated heterocyclic ring whose hetero atoms are 1 or 2 from the group consisting of N, O and S, it furthermore being possible for $R^2$ and $R^3$ or $R^4$ and $R^5$, in each case together, but independently of one another, with the N atom which they substitute, to form a 5- to 8-membered ring which may contain a further hetero atom from the group consisting of N, O and S, and X represents chlorine, bromine, hydroxyl or amino, in a temperature range of from −70° C. to +50° C., preferably −40° C. to +25° C., in liquid phase and in the presence of 0.7–20 equivalents, preferably 1–10 equivalents, of a $C_1$-$C_8$-carboxylic acid to give an open-chain intermediate, followed by a ring-closure reaction with 0.7–12 equivalents, preferably 1–6 equivalents, of a protic acid. or of ammonia in a reaction medium consisting of $C_1$-$C_{10}$-carboxylic acids, halogenated hydrocarbons, alcohols, amides or mixtures thereof.

DETAILED DESCRIPTION OF THE INVENTION

Examples of straight-chain or branched $C_1$-$C_8$-alkyl are methyl, ethyl, propyl, isopropyl, butyl, isobutyl, tert.-butyl, the isomeric pentyls, hexyls, octyls, preferably the $C_1$-$C_4$-alkyl radicals mentioned.

Examples of straight-chain or branched $C_2$-$C_8$-alkenyl are vinyl, propynyl, allyl, the isomeric butenyls, pentenyls, hexenyls or octenyls, preferably the $C_3$-$C_4$-alkenyl radicals mentioned.

Examples of straight-chain or branched $C_2$-$C_8$-alkoxy-alkyl are methoxymethyl, ethoxymethyl and further radicals from the group consisting of $C_3$-$C_9$-alkyl in which a $CH_2$ group has been replaced by an O atom.

Examples of straight-chain or branched $C_3$-$C_8$-alkoxyalk-enyl are methoxyvinyl, ethoxyvinyl, methoxyallyl, 2-methoxypropenyl and others from the group consisting of $C_4$-$C_9$-alkenyl in which a $CH_2$ group has been replaced by an O atom.

Examples of $C_3$-$C_8$-cycloalkyl are cyclopropyl, methylcyclopropyl, dimethylcyclopropyl, cyclobutyl, methylcyclobutyl, cyclopentyl, methyl-cyclopentyl, cyclohexyl, methyl-cyclohexyl, dimethyl-cyclohexyl, cycloheptyl, cyclooctyl, preferably cyclopropyl, cyclopentyl and cyclohexyl, and methyl or dimethyl derivatives thereof.

Examples of $C_6$-$C_{12}$-aryl are phenyl, naphthyl or biphenylyl, preferably phenyl.

Examples of $C_7$-$C_{10}$-aralkyl are benzyl, 1-phenylethyl, 2-phenylethyl and further radicals of this type known to one skilled in the art, preferably benzyl.

The following 5- to 8-membered saturated or unsaturated heterocyclic rings whose hetero atoms are 1 or 2 from the group consisting of N, O and S may be mentioned: pyrrole, furan, thiophene, pyrrolidine, pyrazole, imidazole, thiazole, oxazole, pyridine, pyrimidine, piperazine, which may be substituted on the N atom by $C_1$-$C_4$-alkyl or by hydroxy-$C_1$-$C_4$-alkyl, morpholine, pyran, azepine, azocine, isoxazole, isothiazole, pyridazine and pyrazine. It is known to one skilled in the art that unsaturated heterocyclic rings may display a more or less pronounced aromatic character. Morpholine, pyrrolidine and piperidine, which can be substituted by $C_1$-$C_4$-alkyl or by hydroxy-$C_1$-$C_4$-alkyl, may preferably be mentioned as such saturated or unsaturated heterocyclic rings.

Furthermore, $R^2$ and $R^3$ or $R^4$ and $R^5$ in each case together but independently of one another, with the N atom which they substitute, can form a 5- to 8-membered saturated or unsaturated ring which may contain a further hetero atom from the group consisting of N, O and S. Examples of such rings are the above mentioned heterocycles.

The reaction of the process according to the invention in the case where $R^1$ is methyl, $R^2$ and $R^3$ together with the N atom which they substitute represent morpholine and $R^4$ and $R^5$ denote methyl can be represented by formulae as follows:

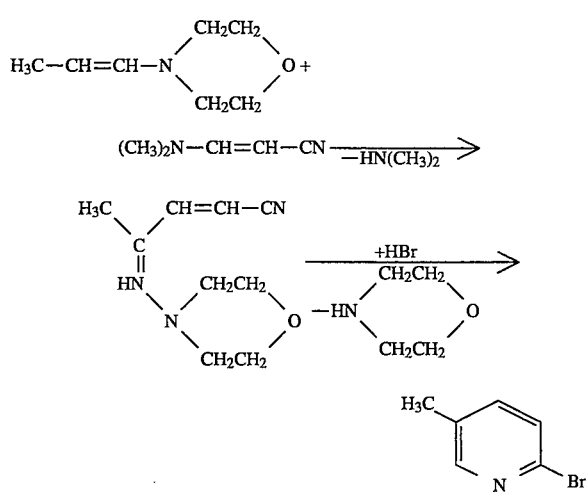

Thus, the enamine and the β-amino-acrylonitrile form, with the elimination of dimethylamine, the 4-$R^1$-5-amino-penta-2,4-dienonitrile shown by way of its formula, which, in the example shown, is cyclised to the 2-bromo-5-methylpyridine by treatment with hydrogen bromide and with elimination of morpholine.

Under the conditions of the reaction according to the invention, an amine exchange can take place between the enamine and the β-amino-acrylonitrile. As a result, morpholine is eliminated in the 1st reaction step leading to the open-chain intermediate, instead of dimethylamine. Consequently, dimethylamine is eliminated in the ring-closure reaction instead of morpholine. This process can be represented by formulae as follows:

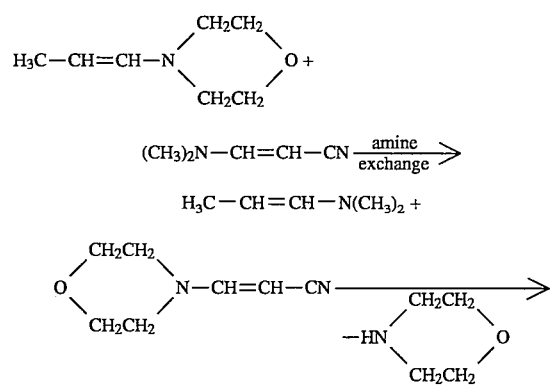

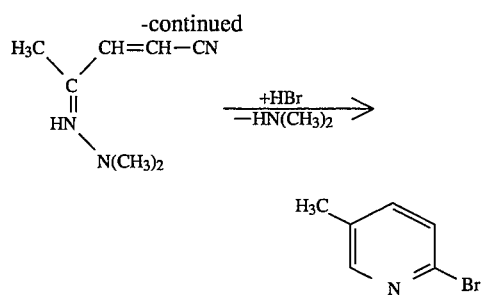

In practice, both forms of the reaction, that is without amine exchange and with amine exchange, will take place side by side. However, this is immaterial to the two-step reaction according to the invention, since, in the final analysis, always both amino groups are eliminated.

Preferably, enamines are used in which the substituent $R^{11}$ which denotes straight-chain or branched $C_1$-$C_8$-alkyl, cyclopropyl, cyclopentyl, cyclohexyl, phenyl or benzyl, takes the place of $R^1$.

Particularly preferably, enamines are used in which the substituent $R^{21}$ which denotes straight-chain or branched $C_1$-$C_4$-alkyl, takes the place of $R^{11}$.

Furthermore, the enamines and β-amino-acrylonitriles preferably used in the process according to the invention are those in which the place of $R^2$, $R^3$, $R^4$ and $R^5$ is taken by the substituents $R^{12}$, $R^{13}$, $R^{14}$ and $R^{15}$ which, independently of one another, denote straight-chain or branched $C_1$-$C_8$-alkyl, cyclopropyl, cyclopentyl, cyclohexyl, phenyl or benzyl, it furthermore being possible for $R^{12}$ and $R^{13}$ or $R^{14}$ and $R^{15}$, in each case together, but independently of one another, with the N atom which they substitute, to form a 5- to 8-membered ring which may contain a further hetero atom from the group consisting of N, O and S.

Furthermore, the enamines and β-amino-acrylonitriles particularly preferably used in the process according to the invention are those in which the place of $R^{12}$, $R^{13}$, $R^{14}$ and $R^{15}$ is taken by the substituents $R^{22}$, $R^{23}$, $R^{24}$ and $R^{25}$ which, independently of one another, denote $C_1$-$C_4$-alkyl, it furthermore being possible for $R^{22}$ and $R^{23}$ or $R^{24}$ and $R^{25}$ in each case together, but independently of one another, with the N atom which they substituted to denote morpholine, pyrrolidine or piperidine, which may be substituted by $C_1$-$C_4$-alkyl or by hydroxy-$C_1$-$C_4$-alkyl.

Enamines for the process according to the invention can be prepared from the underlying aldehydes and the underlying secondary amines in a basically known manner. As a result of its preparation such an enamine may also be associated with a portion of the corresponding aminal. This is immaterial to the success of the process according to the invention.

β-Amino-acrylonitriles are readily available, for example, by reaction of formylacetonitrile salts with secondary amines (EP 18 473) or by condensation of orthoamides with acetonitrile.

The reaction in the process according to the invention takes place in the liquid phase in both steps. If the enamine and the β-amino-acrylonitrile used together form a liquid phase, it is unnecessary to use a solvent. Otherwise, the reaction can be carried out in a solvent from the group of the halogenated hydrocarbons, the ketones, the nitriles, the amides, the esters or the ethers or in a mixture of a plurality of them. Examples of such solvents are: methylene chloride, chloroform, dichloroethane, acetone, methyl ethyl ketone, acetonitrile, dimethylformamide, N-methylpyrrolidone (NMP), N-methyl-caprolactam (NMC), tetramethylurea, methyl acetate, butyl acetate, methyl tert.-butyl ether, tert.-amyl methyl ether, tetrahydrofuran, dioxane, preferably one or more halogenated hydrocarbons. The amount of solvent used is 0 to 2000% by weight, relative to the total amount of enamine and β-amino-acrylonitrile, preferably 50 to 2000% by weight, particularly preferably 200 to 1500% by weight; the lower limit of zero mentioned in the general range of weight percentages denotes in this case the reaction of the enamine with the β-aminoacrylonitrile in liquid phase but without use of an additional solvent of the type mentioned.

The ratio of the two reactants enamine and β-aminoacrylonitrile is chosen in the above mentioned molar range. The ideal value of the molar ratio of the two reactants is obviously close to the value 1:1 but, in most cases, the more expensive component will be used in less than a stoichiometric amount in order to promote, if possible, its complete conversion.

It is immaterial to the success of the process according to the invention which of the reaction components enamine and β-amine-acrylonitrile is introduced first and which is added afterwards; in principle, the simultaneous metered addition of both components is also possible. If a solvent is to be used, it can be either added together with one or both reaction components or else added simultaneously with the addition of one or both reaction components. Addition of the reaction components takes place in the above mentioned temperature range; the reaction is weakly exothermic.

The reaction to give the open-chain intermediate is carried out in the presence of a $C_1$–$C_8$-carboxylic acid, for example in the presence of formic acid, acetic acid, propionic acid, butyric acid, valeric acid, caproic acid or caprylic acid. Preferably, the reaction is carried out in the presence of acetic acid or propionic acid, particularly preferably in the presence of acetic acid. The acid is used in an amount of 0.7 to 20 equivalents, preferably 1 to 10 equivalents, relative to the number of moles of the reaction component used in less than a stoichiometric amount. The carboxylic acid can be diluted with water; for example, a 50% strength acetic acid can be used.

After combining the reaction components and the carboxylic acid, the reaction described above by way of formulae is then allowed to proceed over a period of 0.5 to 24 hours, preferably 1 to 15 hours. The carboxylic acid and the eliminated amine are then separated off from the open-chain intermediate (4-$R^1$-5-amino-penta-2,4-dieno-nitrile) by aqueous workup. This intermediate, which is sparingly soluble in water, is formed in this workup as a solid or by extraction with a water-insoluble solvent is obtained in the form of such an extract. This aqueous workup results in a very elegant manner even when the first reaction step is carried out in the presence of a water-immiscible solvent, for example in the presence of halogenated hydrocarbons. Accordingly, such a procedure is preferred.

The ring-closure reaction to give the 2,5-disubstituted pyridine is carried out using 0.7 to 12 equivalents, preferably 1 to 6 equivalents, of a protic acid or of ammonia. These protic acids can be for example hydrochloric acid, hydrobromic acid, sulphuric acid, phosphoric acid, sulphonic acid or an equivalent strong acid. If hydrochloric acid or hydrobromic acid is used, the substituent X in the 2 position is chlorine or bromine. If other of the protic acids mentioned are used, X becomes hydroxyl. It is very astonishing that ammonia can also be used instead of an acid, the substituent X adopting the meaning of amino in the course of the ring-closure reaction.

Hydrogen halide or ammonia, if introduced in gaseous form, can also be used in an amount exceeding the above values.

The ring-closure reaction in the presence of a protic acid or in the presence of ammonia is carried out in a reaction medium which may have been formed from $C_1$–$C_8$-carboxylic acids, halogenated hydrocarbons, alcohols, amides, further above mentioned acid-resistant solvents or a mixture thereof. Preferably, the reaction is carried out in a mixture of carboxylic acids and halogenated hydrocarbons. The open-chain intermediate, the protic acid or the ammonia and the reaction medium can be combined in any desired order; in ring closure effected by a protic acid, it is preferred to introduce the acid initially and to add the intermediate. The period of time over which the ring-closure reaction takes place is in general 0.1 to 5 hours, this time being of course dependent on the batch size.

EXAMPLES

A) Starting Compounds

Example A1

324.4 g of 90% pure ethylaminal ester (balance DMF), 123 g of acetonitrile and 300 ml of DMF were heated in a 1.3 V4A autoclave at 130° C. for 8 hours. The crude product was distilled (80° C./0.3 mm) giving 187 g of 99.3% pure trans-3-dimethylaminoacrylonitrile (0.45% of DMF; cis-:trans=2:98 according to NMR spectrum), which corresponds to 95.4% of the theoretical yield.

Example A2

60 g of acetonitrile, 60 g of DMF dimethyl acetal, 36 g of pyrrolidine and 150 ml of DMF were refluxed for 8 hours. Removal of volatile components by distillation gave an 87:13 mixture of 3-pyrrolidino- and 3-dimethylaminoacrylonitrile (GC, GC/MS) almost quantitatively in 96% purity.

Example A3

62 g of freshly distilled propionaldehyde were added dropwise with cooling (25° C.) over a period of 40 minutes to 200 g of morpholine and 10 g of potassium carbonate, and the mixture was stirred at 25 to 30° C. for 2 hours. The mixture was concentrated on a rotary evaporator for a short period, and the suspension filtered. The filtrate was subjected to vacuum distillation (30 cm Vigreux column equipped with distillation head); at the beginning the pressure was 30 mbar and towards the end 10 mbar. A product fraction which distilled over at 58° to 65° C. contained 71% of 1-morpholinopropene and 12% of the corresponding aminal (85.8 g, which corresponds to 50.7% of the theoretical yield).

Example A4

108 g of freshly distilled butyraldehyde were added dropwise at 0° C. to a mixture of 213 g of pyrrolidine and 213 g of potassium carbonate. The mixture was allowed to stand overnight at room temperature, diluted with 300 ml of toluene, and the residue was filtered off. The filtrate was then subjected to vacuum distillation at 85° to 90° C. (80 mbar), giving 102 g of 97% pure 1-pyrrolidinobutene, which corresponds to 63.7% of the theoretical yield).

B) Reactions

Example B1

14.1 g of morpholinopropene from A3 were introduced as the initial charge in 50 ml of methylene chloride, and 7.7 g of 3-dimethylaminoacrylonitrile from A1 were added dropwise at +35° C. The mixture was allowed to warm up slowly until reaching 0° C., maintained at 0° C. for 2 hours, and 16 ml of 50% strength acetic acid were added dropwise at room temperature (RT). After stirring at RT for 2 hours, the phases were separated, and the aqueous phase extracted. The concentrated extracts were analysed by GC/MS, and 4-methyl-5-morpholino-penta-2,4-dienonitrile in addition to the corresponding dimethylamino derivative were identified as the main product. Starting compounds and transaminated starting compounds were still present in an amount of 15%.

Example B2

13 g of pyrrolidinobutene from A4 were initially introduced in 50 ml of methylene chloride, and 11.9 g of 3-pyrrolidinoacryionitrile from A2 were added dropwise at −30° C. The subsequent procedure was as described in Example B1, and 4-(1-pyrrolidino-methylene)-2-hexenonitrile was identified by GC/MS as the main product.

Example B3

The crude product from B1 was dissolved in a mixture of 80 ml of acetic acid and 20 ml of chloroform, and dry hydrogen chloride gas was introduced at 0° C. for 30 minutes. Stirring was continued at 0° C. for 1 hour and at 25° C. for 4 hours. The mixture was concentrated, toluene and water were added, and the mixture was brought to a pH of 7–8 with sodium carbonate. The organic phase was separated off, concentrated and subjected to kugelrohr distillation, giving 2-chloro-5-methylpyridine in 37.5% of the theoretical yield. The product was identified by GC and GC/MS comparison with authentic material. H-NMR ($CDCl_3$): 7.22 ($H^3$); 7.48 ($H^4$); 8.62 ($H^6$) ppm.

Example B4

The procedure of B3 was repeated with the crude product from B2. 2-Chloro-5-ethyl-pyridine was obtained in 39.6% and identified by GC/MS coupling and H-NMR.

Example B5

20 ml of concentrated sulphuric acid were added to crude 4-methyl-5-morpholino-2,4-pentadiene prepared analogously to Example 1, and the mixture was then poured onto ice. The reaction product obtained was mainly 2-hydroxy-5-methylpyridine.

Example B6

19.3 g of β-pyrrolidino-acrylonitrile were added at -10° C. to 30 g of pyrrolidino-butene from A4 in 50 ml of chloroform. The mixture was allowed to warmto RT, and 50 ml of acetic acid were added dropwise. After stirring at RT for 15 hours, the mixture was cooled to −10° C., and dry hydrogen chloride gas was introduced. Aqueous workup gave 2-chloro-5-ethylpyridine as the main product.

What is claimed is:

1. A process for the preparation of a 2,5-disubstituted pyridine of the formula

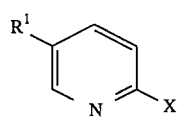

wherein 0.2–5 mol of an enamine of the formula

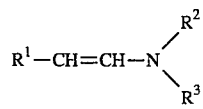

is reacted with 1 mol of a β-amino-acrylonitrile of the formula

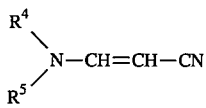

in which formulae $R^1$, $R^2$, $R^3$, $R^4$ and $R^5$ independently of one another, represent straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cyloalkyl $C_6$–$C_{12}$-aryl, $C_7$–$C_{10}$-aralkyl or a morpholine ring, or $R^2$ and $R^3$ or $R^4$ and $R^5$, in each case together but independently of one another, with the N atom which they are attached form a heterocyclic ring. selected from the group consisting of of piperzine, morpholine, pyrrolidine and piperidine optionally substituted on the N atom by $C_1$–$C_4$-alkyl or -hydroxy-$C_1$–$C_4$-alkyl;

X represents chlorine, bromine, hydroxyl or amino, in the temperature range of from −70° C. to +50° C. in liquid phase and in the presence of 0.7–20 equivalents of a $C_1$–$C_8$-carboxylic acid to give an open chain intermediate, followed by a ring-closure reaction with 0.7–12 equivalents of a $C_1$–$C_8$-carboxylic acid, a halogenated hydrocarbon, an alcohol, an amide or a mixture thereof.

2. The process of claim 1, wherein 0.4–3 mol of the enamine is reacted.

3. The process of claim 2, wherein 0.7–1.5 mol of the enamine is reacted.

4. The process of claim 1, wherein the reaction is carried out in a temperature range of −40° C. to +25° C.

5. The process of claim 1, wherein the reaction is carried out in the presence of 1–10 equivalents of a $C_1$–$C_8$-carboxylic acid.

6. The process of claim 1, wherein the ring-closure reaction is carried out with 1–6 equivalents of a proton acid or of ammonia.

7. The process of claim 1, wherein the substituent $R^{11}$, which denotes straight-chain or branched $C_1$–$C_8$-alkyl, cyclopropyl, cyclopentyl, cyclohexyl, phenyl or benzyl, takes the place of $R^1$.

8. The process of claim 7, wherein the substituent $R^{21}$, which denotes straight-chain or branched $C_1$–$C_4$-alkyl, takes the place of $R^{11}$.

9. The process of claim 1, wherein $R^2$, $R^3$, $R^4$ and $R^5$ is taken by substituents $R^{12}$, $R^{13}$, $R^{14}$ and $R^{15}$ which, independently of one another, denote straight-chain or branched $C_1$–$C_8$-alkyl, cyclopropyl, cyclopentyl, cyclohexyl, phenyl or benzyl.

10. The process of claim 9, wherein the place of $R^{12}$, $R^{13}$, $R^{14}$ and $R^{15}$ is taken by the substituents $R^{22}$, $R^{23}$, $R^{24}$ and $R^{25}$ which, independently of one another, denote straight-chain or branched $C_1$–$C_4$-alkyl.

11. The process of claim 1, wherein acetic acid or propionic acid is used as the carboxylic acid for the reaction to give the open-chain intermediate.

12. The process of claim 11, wherein acetic acid is used as the carboxylic acid for the reaction to give the open-chain intermediate.

13. The process of claim 1, wherein a solvent from the group of the halogenated hydrocarbons, the ketones, the nitriles, the amides, the esters and the ethers or a mixture of a plurality thereof is used for adjusting the liquid phase for the reaction to give the open-chain intermediate.

14. The process of claim 13, wherein one or more halogenated hydrocarbons are used.

15. The process of claim 1, wherein the ring-closure reaction is carried out in a mixture of a carboxylic acid and a halogenated hydrocarbon.

* * * * *

UNITED STATES PATENT AND TRADEMARK OFFICE
CERTIFICATE OF CORRECTION

PATENT NO. : 5,466,800
DATED : November 14, 1995
INVENTOR(S) : Kraus, Helmut

It is certified that error appears in the above-indentified patent and that said Letters Patent is hereby corrected as shown below:

Col. 8, line 23    After " attached " insert -- in its place --

Signed and Sealed this

Second Day of April, 1996

Attest:

BRUCE LEHMAN

Attesting Officer    Commissioner of Patents and Trademarks